United States Patent
Frenz et al.

(10) Patent No.: US 7,108,692 B2
(45) Date of Patent: Sep. 19, 2006

(54) APPARATUS FOR APPLYING LIGHT TO A VESSEL WALL

(75) Inventors: Martin Frenz, Münsingen (CH); Beat Ott, Matten (CH)

(73) Assignee: Storz-Endoskop GmbH, (CH)

( * ) Notice: Subject to any disclaimer, the term of this patent is extended or adjusted under 35 U.S.C. 154(b) by 0 days.

(21) Appl. No.: 10/622,685

(22) Filed: Jul. 18, 2003

(65) Prior Publication Data

US 2004/0078032 A1    Apr. 22, 2004

Related U.S. Application Data

(63) Continuation of application No. PCT/EP02/00419, filed on Jan. 17, 2002.

(30) Foreign Application Priority Data

Jan. 19, 2001    (DE) .............................. 101 02 477

(51) Int. Cl.
 *A61B 18/18*    (2006.01)
 *A61B 18/24*    (2006.01)

(52) U.S. Cl. .............................. 606/15; 606/7; 606/18; 607/88; 600/247

(58) Field of Classification Search ............ 606/15–18, 606/7, 10; 607/88, 89; 600/101, 247, 248; 604/19
See application file for complete search history.

(56) References Cited

U.S. PATENT DOCUMENTS

| | | | |
|---|---|---|---|
| 4,600,919 A | 7/1986 | Stern | 340/725 |
| 4,852,567 A * | 8/1989 | Sinofsky | 606/3 |
| 5,104,392 A * | 4/1992 | Kittrell et al. | 606/15 |
| 5,175,616 A | 12/1992 | Milgram | 348/47 |
| 5,242,438 A * | 9/1993 | Saadatmanesh et al. | 606/15 |
| 5,365,370 A | 11/1994 | Hudgins | 359/464 |
| 5,369,736 A | 11/1994 | Kato et al. | 395/125 |
| 5,380,317 A | 1/1995 | Everett et al. | 606/15 |
| 5,415,654 A * | 5/1995 | Daikuzono | 606/15 |
| 5,437,660 A * | 8/1995 | Johnson et al. | 606/15 |
| 5,440,674 A | 8/1995 | Park | 395/123 |
| 5,441,497 A * | 8/1995 | Narciso, Jr. | 606/15 |
| 5,469,535 A | 11/1995 | Jarvis et al. | 395/130 |
| 5,490,240 A | 2/1996 | Foran et al. | 395/130 |
| 5,495,576 A | 2/1996 | Ritchey | 395/125 |
| 5,496,271 A * | 3/1996 | Burton et al. | 607/27 |
| 5,504,845 A | 4/1996 | Vecchione | 395/119 |
| 5,555,366 A | 9/1996 | Teig et al. | 711/169 |
| 5,566,285 A | 10/1996 | Okada | 395/130 |
| 5,611,025 A | 3/1997 | Lorensen et al. | 395/119 |

(Continued)

FOREIGN PATENT DOCUMENTS

DE    101 02 477    7/2002

(Continued)

*Primary Examiner*—A. Farah
(74) *Attorney, Agent, or Firm*—St. Onge Steward Johnston & Reens LLC (57) ABSTRACT

An apparatus for applying light to a site to be treated on a wall of a vessel in the human or animal body, in particular for laser welding of two vessels to one another, has a light-feeding instrument that guides light generated by an extracorporeal light source to the site and radiates it onto the latter. The light-feeding instrument has an elongated optical conductor that can be inserted into the lumen of the vessel and can be displaced therein in the longitudinal direction of the vessel, and has light-deflecting means that direct the light fed through the optical conductor in a substantially radial fashion onto the site to be treated.

37 Claims, 3 Drawing Sheets

U.S. PATENT DOCUMENTS

| | | | |
|---|---|---|---|
| 5,617,322 A | 4/1997 | Yokota | 364/468.04 |
| 5,621,867 A | 4/1997 | Murata et al. | 395/125 |
| 5,748,199 A | 5/1998 | Palm | 345/433 |
| 5,805,205 A | 9/1998 | Songer | 348/56 |
| 5,827,265 A | 10/1998 | Glinsky et al. | 606/8 |
| 5,835,693 A | 11/1998 | Lynch et al. | 345/473 |
| 5,957,917 A * | 9/1999 | Doiron et al. | 606/15 |
| 5,986,662 A | 11/1999 | Argiro et al. | 345/424 |
| 5,988,862 A | 11/1999 | Kacyra et al. | 703/6 |
| 6,023,277 A | 2/2000 | Osaka et al. | 345/419 |
| 6,026,215 A | 2/2000 | Fantone et al. | 358/1.2 |
| 6,066,130 A * | 5/2000 | Gregory et al. | 606/15 |
| 6,084,594 A | 7/2000 | Goto | 345/427 |
| 6,108,005 A | 8/2000 | Starks | 345/419 |
| 6,302,878 B1 * | 10/2001 | Daikuzono | 606/7 |
| 6,313,836 B1 | 11/2001 | Russell et al. | 345/419 |
| 6,572,609 B1 * | 6/2003 | Farr et al. | 606/15 |
| 2003/0060813 A1 * | 3/2003 | Loeb et al. | 606/17 |

FOREIGN PATENT DOCUMENTS

| | | |
|---|---|---|
| EP | 0 761 257 | 3/1997 |
| EP | 0 821 916 | 2/1998 |

\* cited by examiner

Fig.3

APPARATUS FOR APPLYING LIGHT TO A VESSEL WALL

CROSS-REFERENCE TO PENDING APPLICATIONS

The present application is a continuation of pending International patent application PCT/EP02/00419 filed on Jan. 17, 2002, which designates the United States and claims priority of German patent application 101 02 477.0 filed on Jan. 19, 2001.

BACKGROUND OF THE INVENTION

The invention relates to an apparatus for applying light to a site to be treated on a wall of a vessel in the human or animal body, in particular for laser welding of two vessels to one another, having a light-feeding instrument that guides light generated by an extracorporeal light source to the site and radiates it onto the latter.

A general case of application of such an apparatus consists in the application of light to a site to be treated on a wall of a vessel, in order to heal a pathological state, for example a tissue change or a rupture in the vessel wall, at this site.

A special case of application of the apparatus mentioned at the outset to which the following description relates without being restricted thereto is the application of such an apparatus for laser welding of two vessels to one another in order to join the latter to one another end to end or else end to side such that a T-shaped join is produced. Vessels are to be understood as blood vessels such as veins or arteries, or else in the wider sense generally as hollow organs. Such a join of two vessels to one another is required, for example, when a vessel has been ripped open because of injury or because of a surgical resection, or in order to join two vessels opening into one another so as to create a new vessel path or to reconstitute an original one.

In the case of conventional methods for joining two vascular stumps to one another end to end, which is also denoted as anastomosis, the two vascular stumps have been joined to one another by means of conventional suture methods. Such suture methods are, however, time-consuming surgical methods that require experience and skill on the part of the surgeon. Furthermore, when sewing together two vascular stumps there is the risk that an aneurysm, that is to say a weakening of the vessel wall with attendant outward sagging of the vessel wall, will develop at the suture site, or that foreign-body reactions will occur because of the suture material. Moreover, suture joins can frequently only be produced in the case of vessels in open, that is to say invasive operations.

The development of laser surgery has now rendered it possible to replace suture joins by laser welding. It has emerged that laser light of suitable wavelength and suitable power can also be used to "fuse together" tissue of vessels. Successful experiments have already been carried out in vitro for the purpose of welding two vascular stumps end to end. The advantage of the laser treatment as against the conventional suture techniques consists in a lower time outlay and in the avoidance of foreign-body reactions owing to suture material. Moreover, laser welding techniques can also be carried out endoscopically by means of small incisions, that is to say in a minimally invasive fashion.

Although the mechanisms of the laser welding process are not yet completely understood in the case of vascular tissue, it is surmised that the laser light that heats the tissue locally leads to a coagulation of proteins and thus to an anastomotic joining of vascular stumps. However, vessels welded with laser light frequently exhibit insufficient stability of the join that can lead to leaks under the strain of the blood pulsating in the vessel, or even to a complete rupture of the join.

It has therefore been proposed to apply to the junction in advance of the welding a biological solder such as fibrin or albumin in liquid or solid form which penetrates into the tissue to be welded and acts as adhesive during welding. In addition, these are mixed with a chromophore, as absorber, the absorption maximum of which is at the wavelength of the laser light used, in order to launch the laser light optimally into the solder and to release the laser energy there.

A problem is posed, however, by the application of the light in vivo to the site to be treated on the wall of the vessel. When applying the light from the outside of the wall of the vessel, it proves to be difficult to treat such a site on the wall of the vessel that is situated on the side of the vessel averted from the incision. Particularly in the case of laser-aided anastomosis, in which two separated vessels are to be welded to one another, the light-feeding instrument would need to have on the light-exit side an end that can be guided over an entire circumference around the outside of the wall of the vessel. This could be performed, for example, by forceps whose distal end has a cylindrical gripper that can be spread and with the aid of which the vessel is embraced as by forceps, and in which case the light exits circumferentially on the inside of the grippers. However, there is the risk in this case of the vessels collapsing during welding, with the result that the vessel is no longer open for the passage of blood after production of the welded join. Moreover, introducing such an apparatus into the body may require an open invasive operation.

It is therefore the object of the invention to create an apparatus of the type mentioned at the beginning with the aid of which the light can be applied in a minimally invasive way to the site to be treated on the wall of the vessel, and with the aid of which collapse of the vessel upon application of the light is avoided.

SUMMARY OF THE INVENTION

According to the invention, this object is achieved with regard to the apparatus mentioned at the beginning by virtue of the fact that the light-feeding instrument has an elongated light guide that can be inserted into the lumen of the vessel and can be displaced therein in the longitudinal direction of the vessel, and has light-deflecting means that direct the light fed through the light guide in a substantially radial fashion onto the site to be treated.

The apparatus according to the invention renders it possible for the light that is to be applied to the site to be treated from the inside of the wall of the vessel. At a site remote from the site to be treated, the elongated light guide can be inserted like a cannula or a catheter into the lumen of the vessel and displaced therein in the longitudinal direction of the vessel up to the site to be treated. The elongated light guide thus guides the light generated by the extracorporeal light source initially axially along the vessel toward the site to be treated. In the region of the site to be treated, the light-deflecting means provided according to the invention then direct the light axially fed through the light guide onto the site to be treated in a substantially radial fashion. In order that the light guide can be introduced into the lumen of the vessel, the light guide has an appropriate diameter that is smaller than the inside diameter of the vessel. It emerges that the apparatus according to the invention can be used to carry out the application of light to the site to be treated on the wall of the vessel in a minimally invasive fashion. In the case of treatment of a site on a vessel wall, for example in the abdominal aorta, the light guide can be introduced, for example, into the hip artery in the region of the hip and pushed forward to the desired site. The further advantage of the apparatus according to the invention consists in that the light guide inserted into the vessel avoids collapse of the vessel in the region of the treatment site, but keeps the passage of the vessel open. To name two examples, the apparatus according to the invention is particularly suitable for laser-aided anastomosis for joining two vessels to one another end to end or end to side.

In a preferred simple refinement of the apparatus, the light-deflecting means comprise an end of the light guide that is bent approximately at right angles to the remaining longitudinal axis of the light guide.

It is advantageous in this case that the light-deflecting means at the light guide are provided in the form of a distal end thereof that is bent approximately at right angles to the remaining longitudinal axis of the light guide at the light guide itself, as a result of which a very simple refinement of the apparatus in design terms is achieved. In the case when the light guide consists of a single optical fiber, the entire circumference of the wall of the vessel can be irradiated with light by rotating the light guide about its longitudinal axis in the lumen of the vessel. In the case when the light guide consists of a fiber bundle, individual fibers of the fiber bundle could be bent in various radial directions at the distal end, such that the entire circumference of the wall of the vessel could substantially be irradiated with light simultaneously and uniformly without rotation of the light guide about its longitudinal axis.

However, because of the occasionally small diameters of blood vessels, this refinement of the light-deflecting means would result in a tight bending radius of the bent right-angled distal end of the light guide that in particular disturbs the total reflection required for guiding light in the light guide.

In an alternative particularly preferred refinement, it is therefore provided that the light guide is straight at a distal end so that the light emerges substantially axially from the light guide, and that the light-deflecting means direct the light emerging from the light guide in a substantially radial direction toward the site to be treated.

As against the previously described configuration bent at the distal end, the straight configuration at the distal end of the light guide has the advantage that the light guide can be designed overall with a relatively large cross section, as a result of which more light energy can be guided per unit time by the light guide to the site to be treated. The light-deflecting means can, for example, be designed as diffusing elements arranged upstream of the distal end of the light guide.

In a further preferred refinement, the light-deflecting means are designed such that they direct the light emerging from the light guide toward the site to be treated on the wall of the vessel without rotation of the light guide about its longitudinal axis in a fashion distributed uniformly over its entire circumference, in particular in annular fashion.

This measure is specifically of advantage when the entire circumference of the wall of the vessel is to be treated with light, as is the case when two vessels are laser-welded to one another. The laser welding can therefore be carried out with an even lower time outlay, because the entire circumference of the wall of the vessel is simultaneously irradiated with light. Uniform welding of the vessels to one another when seen over the entire circumference of the vessel, something which can be controlled only with difficulty with an light guide that is to be rotated by hand, is achieved at the same time.

In a further preferred refinement, the light-deflecting means are designed as a reflector whose reflecting surface is inclined to the longitudinal direction of the light guide at an angle in the range between 40° and 50°, preferably approximately 45°.

The configuration of the light-deflecting means as a reflector has the advantage that light losses on the basis of absorption or scattering during deflection of the direction of the light can be minimized. The reflective surface can consist, for example, of silver.

It is preferred in this case when the reflecting surface is designed as a conical surface, in particular in the shape of a tipped cone.

This measure constitutes a refinement, simple in design terms, of a reflector which makes it possible to direct the light exiting from the light guide annularly toward the site to be treated on the wall of the vessel without rotation of the light guide about its longitudinal axis in a fashion distributed uniformly over its entire circumference. A tipped-cone configuration has the advantage, moreover, that almost no light losses occur owing to scattering at the tip of the cone.

In a further preferred refinement, the reflecting surface is straight, concavely curved or convexly curved.

The selection of the geometry of the reflecting surface can be used to optimize the light beam directed onto the site to be treated on the wall of the vessel. For example, a concavely shaped reflecting surface can be used to achieve focusing of the light, while a convexly curved reflecting surface can be used to achieve scattering or divergence of the light in order to obtain a relatively wide light patch or light ring on the vessel wall.

In a further preferred refinement, the distal end of the light guide and the light-deflecting means are held immovably relative to one another.

This measure has the advantage that during use of the light-feeding instrument the distal end of the light guide and the light-deflecting means are not displaced, rotated or tilted relative to one another, and it is therefore ensured that the light to be applied always remains directed precisely onto the site to be treated on the wall of the vessel.

In a further preferred refinement, the light-feeding instrument is designed as a catheter.

It is advantageous in this case that the surgeon, usually a vascular surgeon, operating the light-feeding instrument is already accustomed to handling catheters and need not readjust to the handling of the new instrument.

It is preferred in this case when the catheter has a jacket that encases the light guide and is transparent to the light being applied, at least in the region of the light-deflecting means.

It is advantageous in this case that the light to be applied can pass without attenuation through the jacket forming the casing of the catheter, and can be irradiated onto the site to be treated with the desired power set substantially at the light source.

It is further preferred when the distal end of the light guide and the light-deflecting means are arranged in a tube that connects the two and is transparent to the light to be applied.

This measure constitutes a simple design possibility for permanently and immovably connecting to one another the light-deflecting means in the form of the preferably conical reflector and the distal end of the light guide. The transparent tube can be fabricated, for example, from Perspex.

In a further preferred refinement, the light-feeding instrument has holding means for fixing the vessel, in particular for fixing vessels to one another, during the application of light.

Particularly in the case of joining two vessels to one another by laser welding, it is necessary to fix the two vessels to one another during the application of light until adequate fusing together has taken place. Owing to the previously mentioned holding means provided on the instrument, fixing therefore requires no sutures that have proved to be disadvantageous, as mentioned at the beginning. The holding means can comprise, for example, a vascular stent surrounding the instrument such as is frequently used in vascular surgery.

In a particularly preferred refinement, the holding means have, however, a balloon that extends axially beyond the distal end of the light guide and beyond the light-deflecting means and surrounds the light guide and the light-deflecting means.

The instrument according to the invention is therefore preferably designed as a balloon catheter, the balloon serving the purpose of fixing the two vessels to one another for the welding operation. Moreover, the balloon permits the two vessels to be aligned with one another very precisely, for example in the case of an end-to-end join, without axial offsetting, it thereby being possible to produce a very clean weld between the vessels. The diameter of the balloon is preferably selected such that it is slightly larger than the inside diameter of the lumen of the vessels, as a result of which the vessels can be fixed permanently and immovably on the balloon.

In a further preferred refinement, the balloon has an elongated straight or T-shaped geometry.

With the aid of an elongated straight shape of the balloon, two vessels can be fixed to one another for an end-to-end join in a precise axial alignment relative to one another for the purpose of the welding operation, while two vessels can be fixed effectively to one another end to side by a T-shaped geometry of the balloon.

It is particularly preferred in this case when the balloon can be dilated.

This has the advantage, firstly, that the balloon can be adapted to various diameters of the lumina of vessels by dilating to a different extent, that is to say expanding by means of a fluid, for example, while secondly this measure has the advantage that the diameter of the balloon can be reduced by letting out the fluid for the operation of inserting the catheter into the vessel and for withdrawing it from the vessel, as a result of which the instrument can very easily be displaced in the vessel and, in particular, be inserted into the vessel, and removed there from again, by a very small incision. A balloon that can be filled with a fluid, for example water, has, moreover, the advantage of cooling.

It is preferred, furthermore, when an outer side of the balloon consists of a material that does not adhere to biological tissue.

This advantageously avoids the vascular tissue "caking on" the balloon during treatment of the vessel wall with light, in particular during welding of two vascular stumps. After termination of the treatment operation, the balloon can therefore be detached from the vessel wall without a problem.

In a further preferred refinement, the catheter is flexible.

It is advantageous in this case that the light-feeding instrument can also be inserted into non-straight vessel curves and be displaced axially therein.

In a further preferred refinement, the light guide has a single optical fiber.

With a single optical fiber, the light-feeding instrument according to the invention, particularly when configured as a catheter, can be constructed with a very small diameter, and can have a corresponding flexibility. The optical fiber is preferably a glass fiber customary for laser applications. The use of a single optical fiber as light guide has the advantage, moreover, that the radiation of the light from the optical fiber can be concentrated onto a very small spot, and can therefore be controlled very precisely.

In a further preferred refinement, the light source generates light whose wavelength is in a wavelength region between 780 nm and 2100 nm, and preferably is 808 nm or 2010 nm.

The inventors carried out experiments on welding vascular stumps to one another, and these experiments proved to be particularly advantageous for anastomosis of vessels with reference to the required welding duration, the tensile strength, the density, rupture strength and the tissue damage for the cited wavelengths and the cited powers of the laser light, particularly good results being achieved in conjunction with a tissue adhesive, for example fibrin or albumin.

Further advantages and features emerge from the following description and the attached drawing.

It goes without saying that the abovementioned features and those still to be explained subsequently can be used not only in the respectively specified combination, but also in other combinations, or on their own, without departing from the scope of the present invention.

BRIEF DESCRIPTION OF THE DRAWINGS

Exemplary embodiments of the invention are illustrated in the drawing and will be described in more detail hereafter with reference to it, in which:

FIGS. 3a) to 3c) show a schematic illustration of the application of the apparatus in FIGS. 1 and 2 in three partial images for welding two vessels to one another.

DETAILED DESCRIPTION OF PREFERRED EMBODIMENTS

Figures 1, 2:
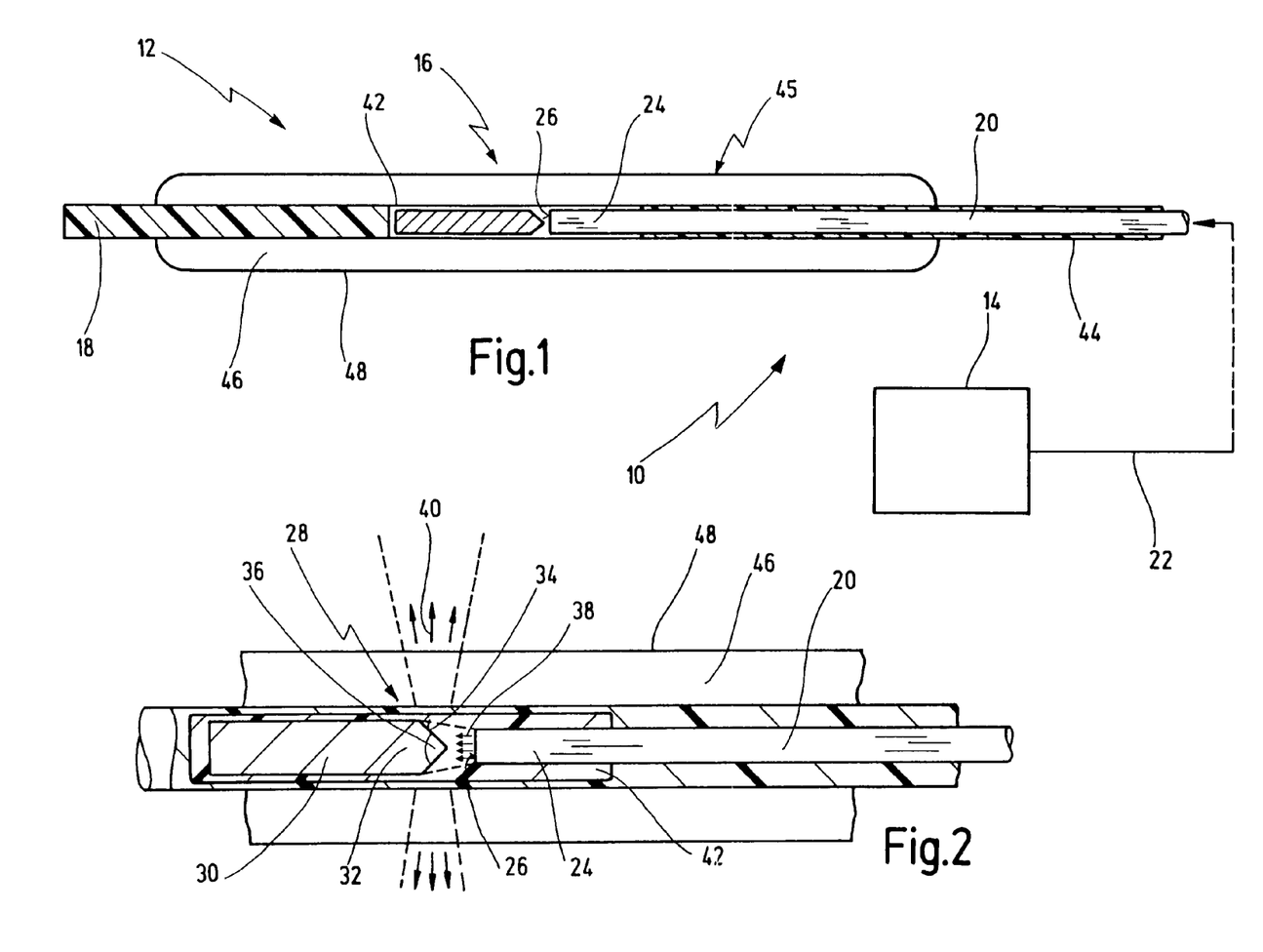
FIG. 1 shows a schematic partial illustration of an apparatus for applying light to a site to be treated on a wall of a vessel in the human or animal body, in side view, partially in longitudinal section.
FIG. 2 shows an enlarged section of the apparatus in FIG. 1.

Illustrated schematically in FIG. 1 is an apparatus, represented with the aid of the general reference numeral 10, for applying light to a site to be treated on a wall of a vessel in the human or animal body, in particular for laser welding of two vessels to one another.

The apparatus 10 has a light-feeding instrument 12 that guides light generated by an extracorporeal light source 14 to the site to be treated. The illustration of the instrument 12 and the light source 14 is not true to scale, rather the instrument 12 is illustrated in a greatly enlarged fashion in relation to the light source 14.

The light-feeding instrument 12 is designed as a catheter 16. The distal end 18 of the catheter 16 forms the catheter tip. The catheter 16 is designed such that it can be inserted into the lumen of a vessel, for example a vein or an artery, and can be displaced therein in the longitudinal direction of the vessel. The distal end 18 of the catheter 16 can also be designed with a tip in order that it can be lanced into the lumen of the vessel through the vessel wall.

The instrument 12 has an elongated light guide 20 that is designed as a single optical fiber. The light guide 20 can, however, also be a bundle of optical fibers. The optical fiber forming the light guide 20 is a glass fiber.

The light generated extracorporally in the light source 14, for example laser light, is, for example, launched extracorporally into the light guide 20 via a diagrammatically illustrated optical cable 22 that is connected to the catheter 16 at the proximal end thereof (not illustrated in more detail).

A distal end 24 of the light guide 20 is of straight design. Consequently, light guided through the light guide 20 from the proximal to the distal ends emerges substantially axially from an end face 26 of the light guide.

The light-feeding instrument further has light-deflecting means 28 that deflect the light fed through the light guide substantially radially, and thus transverse to the longitudinal direction of the light guide 20.

The light-deflecting means 28 are designed as a reflector 30 that is formed by a cylindrical element whose proximal end 32 facing the distal end 24 of the light guide 20 has a reflector surface 34. The reflecting surface 34 is designed as a conical surface, as the lateral surface of a tipped cone in the exemplary embodiment shown.

Whereas the reflecting surface 34 as the lateral surface of a tipped cone is straight in the exemplary embodiment shown, the conical surface can also be curved concavely to focus the reflecting light, or be curved convexly to scatter the light.

Whereas the body of the reflector 30 can be formed from plastic, the reflector surface 34 has a material with a high reflection coefficient, for example silver.

The reflector surface 34 has an aperture angle 36 of approximately 90°, such that the reflecting surface 34 is inclined to the longitudinal direction of the light guide 20 at an angle of approximately 45°.

Because of the configuration of the reflecting surface 34 as a conical surface, the light exiting essentially axially from the end face 26 of the light guide 20 (arrows 38) is deflected over a full circumference of 360°, that is to say to all sides, in a substantially radially annular fashion of uniform distribution.

The dimensions of the light guide 20 and of the reflecting surface 34 of the reflector 30 are dimensioned such that the light reflected in accordance with the arrows 40 strikes the wall of the vessel annularly in that state of the catheter 16 used in the vessel, the annular strip having a width of approximately 1 to 5 mm.

The light-deflecting means 28, in the form of the reflector 30, and the distal end 24 of the light guide 20 are held immovably relative to one another. For this purpose, the reflector 30 and the distal end 24 of the light guide 20 are arranged in a tube 42 connecting the two and transparent to the light to be applied. The tube 42 preferably consists of Perspex.

The catheter 16 also has a jacket 44 which surrounds the light guide 20 from the distal end 24 up to the proximal end. The jacket 44 merges at the distal end into the distal end 18 of the catheter 16, and is designed there as solid material. The jacket 44 can consist of materials customary for catheters, the jacket 44 being, however, transparent to the light to be applied, at least in the region of the light-deflecting means 28, that is to say in the region of the reflecting surface 34. Outside this region, the jacket 44 and also the tube 42 could consist of a light-absorbing material, in particular could be black, in order to avoid disturbing reflections that can damage tissue that is not involved.

The light-feeding instrument 12 also has holding means 45 in the form of a balloon 46 that extends axially beyond the distal end 24 of the light guide 20 and beyond the light-deflecting means 28, and surrounds the light guide 20 and the light-deflecting means 28.

The balloon 46 has an envelope 48 which is, in turn, transparent to the light to be applied, at least in the region of the light-deflecting means 28.

Moreover, the balloon 46 can be dilated, that is to say expanded, the balloon 46 being illustrated in its dilated state in FIG. 1. The fluid inlet required for dilating the balloon 46, and the fluid outlet required for running off the fluid are not illustrated in the schematic illustration. In the state without fluid, the balloon 46 collapses or, when the envelope 48 is of appropriately elastic design, it is drawn correspondingly together such that the balloon 46 is then greatly reduced in diameter. In the dilated state, the balloon 46 has an elongated straight cylindrical shape that is suitable for fixing two vessels to one another end to end.

Figure 4:
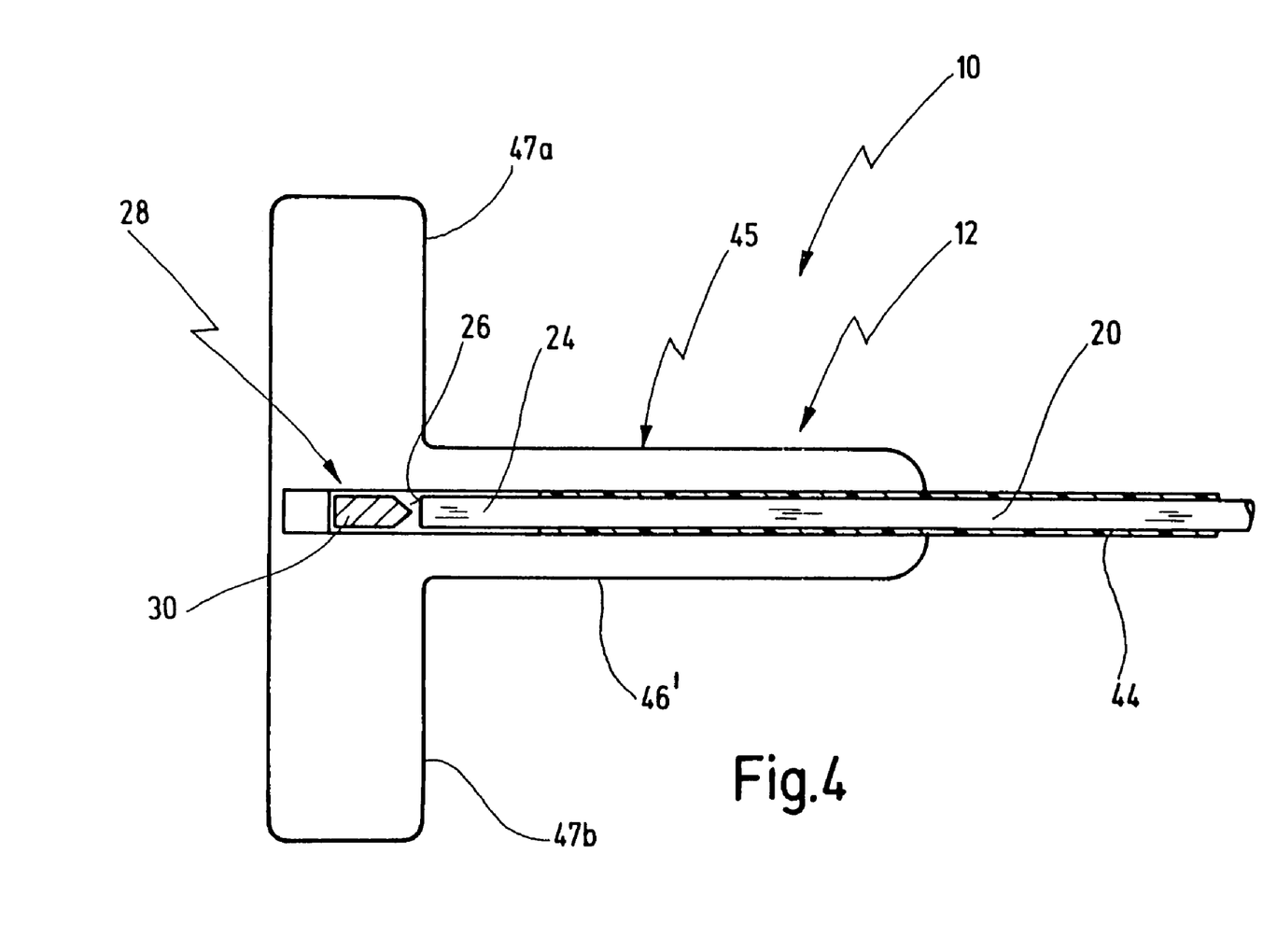
FIG. 4 shows a schematic partial illustration of an exemplary embodiment modified by comparison with FIG. 1.

An exemplary embodiment modified by comparison with FIG. 1 is illustrated in FIG. 4 and is suitable for fixing two vessels end to side. Identical or corresponding parts have been provided in FIG. 4 with identical reference numerals. The holding means 45 of the instrument 12 in FIG. 4 have a dilatable balloon 46' that is of T-shaped design. Two arms 47a and 47b of the balloon 46' run transverse to the longitudinal direction of the light guide 20, in order in the case of a joining of two vessels end to side to engage in the second vessel, which runs transverse to the first vessel, in order to fix said second vessel to the other vessel during welding.

Referring again to FIGS. 1 and 2, an outer side of the envelope 48 of the balloon 46 is produced from a material that does not adhere to biological tissue.

The light-feeding instrument 12 is flexible as a whole, and so it can be adapted to the course of the vessel into which the instrument 12 is inserted.

The light source 14 preferably generates light in a wavelength region between 780 nm and 2100 nm.

A semiconductor diode laser can be used to generate light with the wavelength 808 nm, and a diode-pumped Ho: YAG laser can be used to generate light with a wavelength of 2010 nm.

Described below is a method for the laser welding of two vascular stumps to one another in which the apparatus 10 is used. However, it goes without saying that the apparatus 10 can also be used for other treatments of vessels with light.

Figure 3:
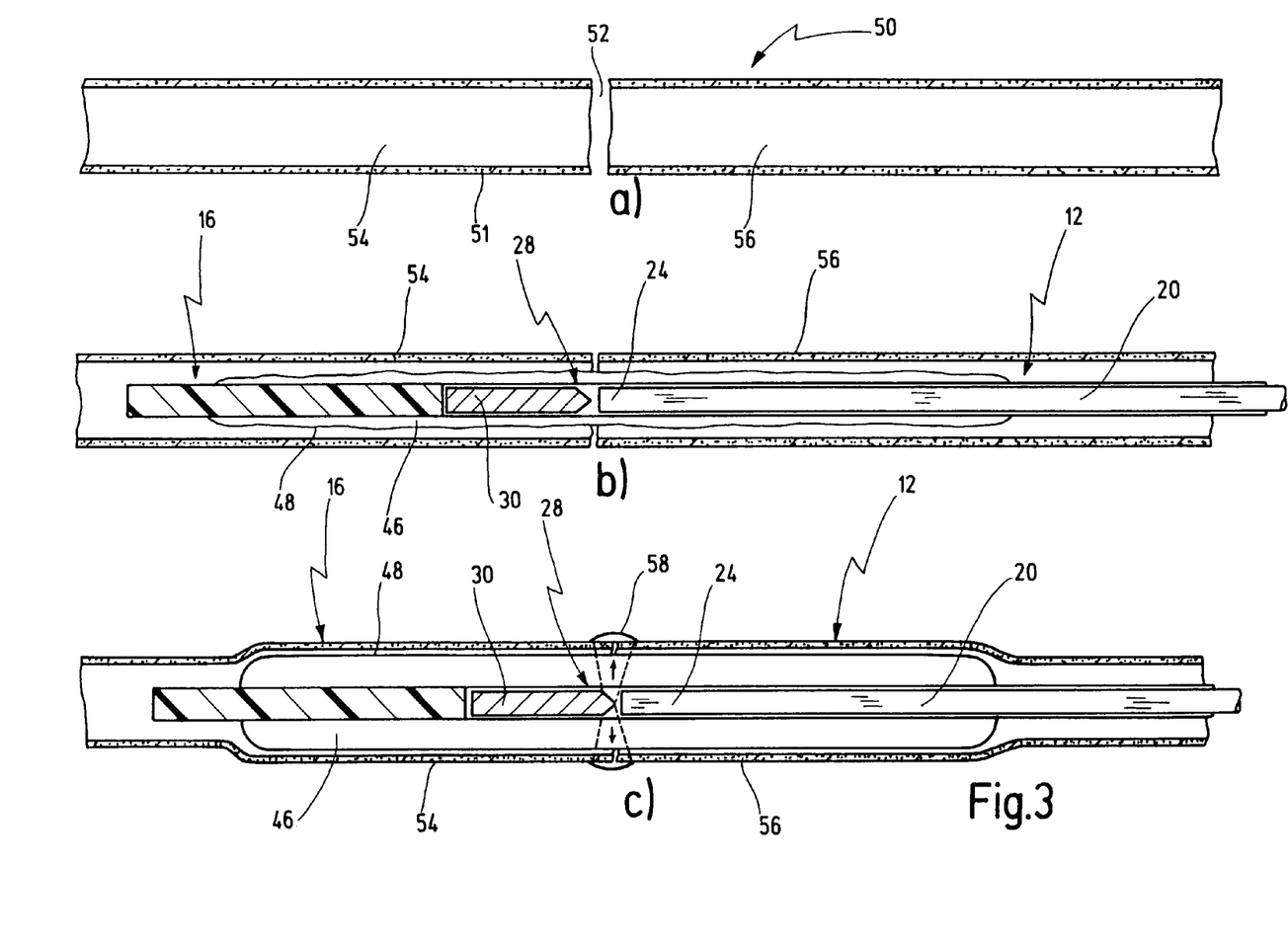

Illustrated schematically in FIG. 3a) is a vessel 50 with a wall 51 that is completely severed along a parting line 52. The aim of the method described below is to weld the corresponding vessels or vascular stumps 54 and 56 to one another at the parting line 52 by means of laser light.

Generally speaking, the method consists in guiding the laser light required for the welding through the lumen of the vessel 50 along the latter as far as the site to be treated, which is formed here by the parting line 52, and there directing the axially fed light in a radial direction onto the site to be treated.

The vascular stumps 54 and 56 are fixed to one another before the application of light.

The previously described apparatus 10 with the instrument 12 is suitable for carrying out the method.

The instrument 12 designed as a catheter 16 is firstly inserted into the lumen of the vessel with its distal end 18 in front at a site at a spacing from the site to be treated (parting line 52). The catheter 16 is preferably inserted by means of a small incision, preferably where the vessel 50 to be treated runs close to the surface of the body. In the case when the vessel 50 is the abdominal aorta, the catheter 16 can be inserted, for example, in the region of the hip artery, which runs close to the surface of the body. For this purpose, the catheter 16 has a corresponding length in order to be pushed forward from the incision site through the lumen of the vessel 50 in the longitudinal direction of the latter as far as the site to be treated (parting line 52).

The instrument 12 is pushed forward in the lumen of the vessel 50 until the light-deflecting means 28 come to lie at the level of the site to be treated, that is to say, here, the parting line 52, as is illustrated in FIG. 3b).

The balloon is evacuated as the instrument 12 is pushed forward, as is likewise illustrated in FIG. 3b)

As soon as the instrument 12 is brought to the spot as in FIG. 3b), the balloon 46 extends both in the vascular stump 54 and in the vascular stump 56 over an adequate partial length of said stumps.

As soon as the instrument 12 is brought to the spot, as illustrated in FIG. 3b), the balloon 46 is dilated by means of suitable devices that are provided on the instrument 12 and can be operated extracorporally, such that the balloon 46 assumes the state illustrated in FIG. 3c).

The balloon 46 can preferably be dilated until its outside diameter is slightly larger than the inside diameter of the lumen of the vessel 50, such that the vessel 50 is somewhat expanded radially in the region of the balloon 46. In this way, the vascular stumps 54 and 56 are immovably fixed on the balloon 46 and thus on the instrument 12, and are aligned exactly relative to one another without an axial offset.

The vascular stumps 54 and 56 are pushed together as close to one another as possible along the parting line 52.

It is now possible to start the laser welding. For this purpose, the light source 14 is switched on, and the light generated by the light source 14 is guided along the light guide 20 in the vicinity of the site to be treated in the wall of the vessel 50, that is to say in the vicinity of the parting line 52, exits there from the distal end 24 of the light guide 20, and is directed onto the tissue of the wall of the vessel 50 in a small region on both sides of the parting line 52 via the light-deflecting means 28 in a substantially radial fashion, specifically distributed uniformly over the entire circumference of the parting line 52. In this case, the light enters the tissue of the wall of the vessel 50 through the balloon 46.

Laser light with a wavelength of 2010 nm is used if the work is performed without a biological solder. The spot diameter of the light striking the tissue of the vessel 50 has a size of approximately 4 mm in the axial direction of the vessel 50. The duration of irradiation is between approximately 50 s and 140 s until the tissues of the vascular stumps 54 and 56 are fused together.

When use is made of laser light of a wavelength of 808 nm, before the irradiation with light a biological solder 58, for example albumin, is applied in advance, for example with the aid of a syringe, in the region of the parting line 52 from the outside of the vessel 50. The solder is suitable for coagulating with the tissue of the vessel 50 through the absorption of light, and thus for amplifying the desired binding effect. At this wavelength, the laser light penetrates the vessel wall substantially without absorption, and is completely absorbed by the solder 58.

It follows from the foregoing description that by means of the apparatus 10 according to the invention and the instrument 12 according to the invention the method for laser welding of two vessels to one another by irradiating light from the lumen of the vessel in a uniformly radial fashion to all sides firstly permits a shortening of the duration of treatment, and secondly allows the light to act uniformly overall.

What is claimed is:

1. An apparatus for applying light to a site to be treated on a wall of a vessel in the human or animal body, comprising:
    a light-feeding instrument designed to guide light generated by an extracorporal light source to said site and to radiate said light onto said site;
    said light-feeding instrument comprising
    an elongated light guide that can be inserted into said vessel and can be displaced therein in a longitudinal direction of said vessel; and
    light-deflecting means designed to direct said light fed through said light guide in a substantially radial direction onto said site to be treated;
    wherein said light-deflecting means are designed as a reflector whose reflecting surface is inclined to a longitudinal direction of said light guide, and wherein said reflecting surface is designed such that said light emerging from said light guide is reflected toward said site to be treated on said wall of said vessel in a fashion distributed uniformly over an entire circumference of said wall without rotation of any one of said light guide and said reflector about its longitudinal; and
    holding means for fixing said vessel during the application of said light, said holding means having a balloon that extends axially beyond a distal end of said light guide and beyond said light-deflecting means and surrounds said light guide and said light-deflecting means.

2. The apparatus of claim 1, wherein said light guide is straight at a distal end so that said light emerges substantially axially from said light guide, and wherein said light-deflecting means direct said light emerging from said light guide in a substantially radial direction toward said site to be treated.

3. The apparatus as claimed of claim 1, wherein said light-deflecting means are designed such that they direct said light emerging from said light guide toward said site to be treated on said wall of said vessel in annular fashion.

4. The apparatus of claim 1, wherein said reflecting surface of said reflector is inclined with respect to a longitudinal axis of said light guide at an angle in the range between 40° and 50°.

5. The apparatus of claim 4, wherein said reflecting surface is designed as a conical surface.

6. The apparatus of claim 1, wherein said reflecting surface of said reflector is inclined with respect to a longitudinal axis of said light guide at an angle in the range between 40° and 50°, and wherein said reflecting surface has a geometry chosen from the group comprising a straight, concavely curved or convexly curved geometry.

7. The apparatus of claim 1, wherein a distal end of said light guide and said light-deflecting means are held immovably relative to one another.

8. The apparatus of claim 1, wherein said light-deflecting means are formed by a distal end of said light guide that is bent approximately at right angles to a longitudinal axis of said light guide.

9. The apparatus of claim 1, wherein said light-feeding instrument is designed as a catheter.

10. The apparatus of claim 9, wherein said catheter has a jacket that encases said light guide and is transparent to said light to be applied, at least in the region of said light-deflecting means.

11. The apparatus of claim 1, wherein a distal end of said light guide and said light-deflecting means are arranged in a tube that connects the two and is transparent to said light to be applied.

12. The apparatus of claim 1, wherein said balloon has an elongated geometry chosen from the group comprising a straight or T-shaped geometry.

13. The apparatus of claim 1, wherein said balloon can be dilated.

14. The apparatus of claim 1, wherein an outer side of said balloon consists of a material that does not adhere to biological tissue.

15. The apparatus of claim 1, wherein said balloon is transparent to said light to be applied at least in the region of said light-deflecting means.

16. The apparatus of claim 1, wherein said light-feeding instrument is flexible.

17. The apparatus of claim 1, wherein said light guide has a single optical fiber.

18. The apparatus of claim 1, wherein said light source generates light whose wavelength is in a wavelength range between 780 nm and 2100 nm.

19. The apparatus of claim 1, wherein said light source generates light whose wavelength is chosen from the group comprising the wavelength 808 nm or 2010 nm.

20. The apparatus of claim 1, wherein it can be used for laser welding two vessels to one another.

21. An apparatus for applying light to a site to be treated on a wall of a vessel in the human or animal body, comprising:
a light-feeding instrument designed to guide light generated by an extracorporal light source to said site and to radiate said light onto said site;
said light-feeding instrument comprising
an elongated light guide that can be inserted into said vessel and can be displaced therein in a longitudinal direction of said vessel; and
light-deflecting means designed to direct said light fed through said light guide in a substantially radial direction onto said site to be treated;
wherein said light-deflecting means are designed as a reflector whose reflecting surface is inclined to a longitudinal direction of said light guide, and wherein said reflecting surface has an extension in circumferential direction about said longitudinal direction of said light guide such that said light emerging from said light guide is reflected toward said site to be treated on said wall of said vessel in a fashion distributed uniformly over an entire circumference of said wall without rotation of said light guide about its longitudinal axis; and
holding means for fixing said vessel during the application of said light, said holding means having a balloon that extends axially beyond a distal end of said light guide and beyond said light-deflecting means and surrounds said light guide and said light-deflecting means.

22. The apparatus of claim 21, wherein said light guide is straight at a distal end so that said light emerges substantially axially from said light guide.

23. The apparatus of claim 21, wherein said reflecting surface is designed as a conical surface.

24. The apparatus of claim 21, wherein said reflecting surface is inclined with respect to a longitudinal axis of said light guide at an angle in a range between 40° and 50°.

25. The apparatus of claim 21, wherein said reflecting surface is chosen from the group comprising a straight, concavely curved or convexly curved geometry.

26. The apparatus of claim 21, wherein a distal end of said light guide and said reflector are held immovably relative to one another.

27. The apparatus of claim 21, wherein said light-feeding instrument is designed as a catheter.

28. The apparatus of claim 27, wherein said catheter has a jacket that encases said light guide and is transparent to said light to be applied, at least in the region of said reflector.

29. The apparatus of claim 21, wherein said light-feeding instrument is designed as a catheter, and wherein a distal end of said light guide and said reflector are arranged in a tube that connects the two and is transparent to said light to be applied.

30. The apparatus of claim 21, wherein said balloon has an elongated geometry chosen from the group comprising a straight or T-shaped geometry.

31. The apparatus of claim 21, wherein said balloon can be dilated.

32. The apparatus of claim 21, wherein said balloon is transparent to said light to be applied at least in the region of said light-deflecting means.

33. The apparatus of claim 21, wherein said light-feeding instrument is flexible.

34. The apparatus of claim 21, wherein said light guide has a single optical fiber.

35. The apparatus of claim 21, wherein said light source generates light whose wavelength is in a wavelength range between 780 nm and 2100 nm.

36. The apparatus of claim 21, wherein said light source generates light whose wavelength is chosen from the group comprising the wavelength 808 nm or 2010 nm.

37. The apparatus of claim 21, wherein it can be used for laser welding two vessels to one another.

* * * * *